United States Patent [19]

Carrier et al.

[11] Patent Number: Plant 7,648

[45] Date of Patent: Sep. 10, 1991

[54] ALSTROEMERIA NAMED LEONA

[75] Inventors: Leonard E. Carrier, Encinitas, Calif.; Stephen Garton, West Jordan, Utah

[73] Assignee: Native Plants, Inc., Salt Lake City, Utah

[21] Appl. No.: 512,806

[22] Filed: Apr. 20, 1990

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Venable, Baetjer, Howard & Civiletti

[57] ABSTRACT

This plant is particularly characterized by its drawf habit which makes the plant eminently suitable for cultivation as a potted plant. In addition, the plant bears several flowering stalks which carry large attractive flowers which are predominantly of a lavendar-purple coloration. The attractive flowers and desirable growth habit of this plant provide a novel addition to the range of Alstroemerias.

1 Drawing Sheet

BACKGROUND OF THE NEW PLANT

This new variety of Alstroemeria originated as a seedling resulting from crossing two plants growing among a collection of breeding stock maintained in a greenhouse in Encinitas, Calif. The seedling was selected for further propagation and testing because of the dwarf characteristic of the whole plant, and the attractive color of the many large flowers contained in several inflorescences as the plant bloomed in a pot. The select plant was propagated in Salt Lake City, Utah by division of the rhizomatous rootstock and through tissue culture. The distinguishing characteristics of the new plant hold true in successive vegetative generations and appear to be firmly fixed. Propagation work is currently being carried out in Salt Lake City using tissue culture methods.

DESCRIPTION OF THE DRAWING

This new variety of Alstroemeria plant is illustrated by the accompanying photographic drawing in full color showing a blooming umbel of the plant with buds and flowers in different stages of flower development. The color renditions are believed to be as close to the specified color as is possible to obtain by conventional photographic procedures.

DESCRIPTION OF THE NEW PLANT

The following is a detailed description of the new Alstroemeria variety with color designations according to the R.H.S. Colour Chart of The Royal Horticultural Society of London, England. The observations were made on plants grown in a greenhouse in Utah County, Utah, during the summer.

THE PLANT

Origin: Seedling (73-LOP-80A).

Parentage:

*Seed parent.*—Breeding stock plant No. LOP.

*Pollen parent.*—Breeding stock plant No. 80A.

Classification: Alstroemeria hybrid.

Form: Compact, erect bush with a slightly spreading habit having several flower stalks bearing branches with simple umbel arrangement at the tops.

Height: About 40 cm.

Growth: Profuse and vigorous.

Rootstock: Rhizomatous, the rhizomes bear numerous buds which give rise to vegetative and reproductive shoots throughout the growth period. Rhizomes also produce roots some of which become tuberous.

Foliage:

*Quantity.*—Abundant with 20 to 30 leaves per stem.

*Leaf size.*—Usually 10 to 13 cm. long and 2.5 to 3.0 cm. wide.

*Leaf shape.*—Elliptical.

*Texture.*—Waxy.

*Color.*—Upper surface — Dark green. Lower surface — Light grey-green.

THE BUD

Form: Pear-shaped. The six petals are perianth and there is no calyx.

Size: Medium.

*Diameter.*—1.5 cm.

*Length.*—3.0–4.0 cm.

Length of peduncle: 2.0–5.0 cm.

THE FLOWER

Blooming habit: Continuous and freely flowering throughout the season.

Flower size: Large.

*Diameter.*—About 6.5 cm.

*Length.*—About 5.5 cm.

Shape: Generally funnel-like.

Borne: Singly.

Petalage:

*Number.*—Six.

*Arrangement.*—Two concentric circles of three.

*Form.*—Outer petals — Obcordate. Inner petals — Elliptical.

*Texture.*—Smooth.

*Appearance.*—Satiny.

*Color.*—Outer petals: General color is of the violet group, 84C, with a purple 78B, patch in the middle of the upper half of the petals. At the middle of the upper margin there is a small green, 141A, protruberance where 4–6 green ribs originate and pass through a lighter colored region to the purple patch. The reverse surfaces of these petals are of the violet group, 84C, with green venation visible in the upper parts. Inner petals: Upper;

The tip of the upper margin is green 141A. The upper portion is pale purple, 76D. In the middle section is a yellow spot, 2B. The basal portion is light purple, 76C. These petals are marked with numerous dark, greyed-purple, streaks, 187A, which extend from the base almost to the tip. The distal portions of the reverse surfaces are violet, 84B, middle sections are yellow green, 154B, and the basal portions are violet, 84C. Streaks on the upper surface are visible through the petal. Lower; The body of the petal is pale purple, 76D, with a central violet colored area, 84B. The tip of the upper margin is green. The petal has few greyed-purple streaks 187A. The reverse surface is violet, 84C, with longitudinal veins. A purple color, 78B, is intraveinal.

Persistence: The flowers hang and dry.

Lasting quality: On the plant, 14–18 days.

Main stem or stalk:

*Length.*—40 to 50 cm.

*Color.*—Medium green.

*Character.*—Strong and upright.

REPRODUCTIVE ORGANS

Stamens:

*Number.*—Six.

*Arrangement.*—One opposite each petal.

*Anthers.*—Size: 8 mm. Color: Dark grey-green.

*Filaments.*—Length: About 4 cm. Color: Lavender-pink.

*Pollen.*—Color: Dary grey-green.

Pistils:

*Number.*—One.

*Style.*—Length: About 4 cm. Color: Violet.

*Stigma.*—Color: Violet.

Fruit:

*Shape.*—Capsular.

*Color.*—Light brown at maturity.

What is claimed:

1. A new and distinctive Alstroemeria hybrid, substantially as shown and described herein, characterized by a dwarf habit and large lavender-purple colored flowers which are borne in attractive inflorescences on relatively dwarf flower stalks.

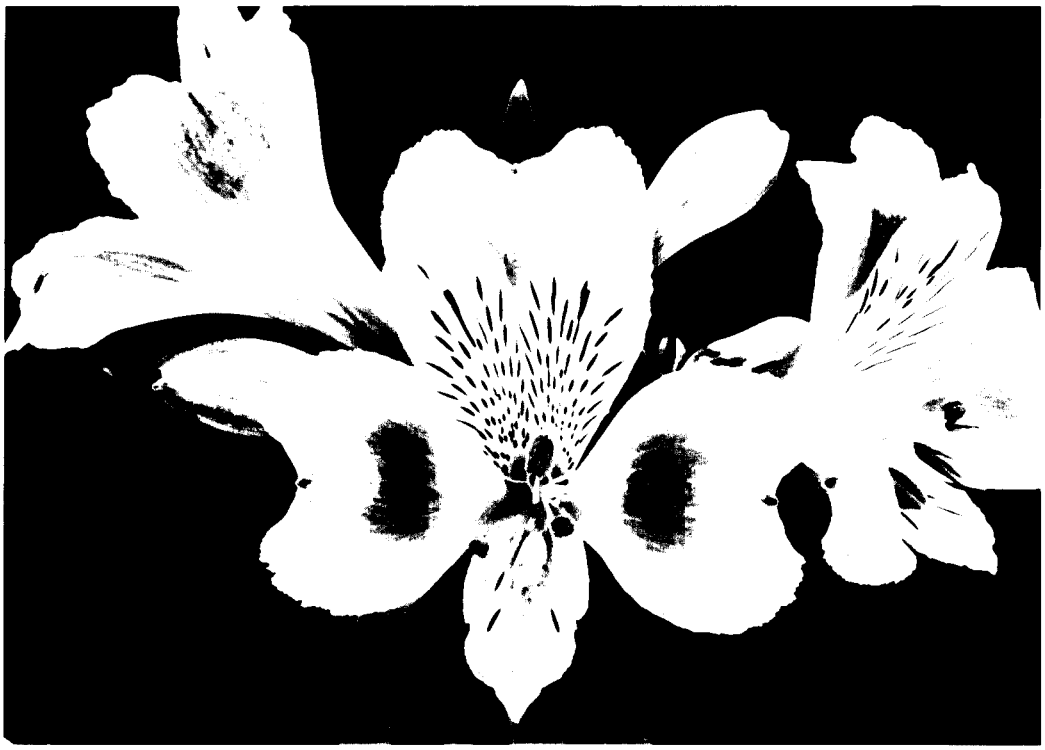

* * * * *